United States Patent [19]

Dessauer

[11] 4,311,783
[45] Jan. 19, 1982

[54] DIMERS DERIVED FROM UNSYMMETRICAL 2,4,5,-TRIPHENYLIMIDAZOLE COMPOUNDS AS PHOTOINITIATORS

[75] Inventor: Rolf Dessauer, Greenville, Del.

[73] Assignee: E. I. Du Pont de Nemours and Company, Wilmington, Del.

[21] Appl. No.: 169,735

[22] Filed: Jul. 17, 1980

Related U.S. Application Data

[62] Division of Ser. No. 66,373, Aug. 14, 1979, Pat. No. 4,252,887.

[51] Int. Cl.$^3$ .......................... G03C 1/72; G03C 1/52
[52] U.S. Cl. ..................... 430/270; 430/905; 430/915; 430/916; 430/917; 430/920; 430/292; 430/293; 430/334; 430/358; 430/346
[58] Field of Search ............... 430/293, 334, 358, 346, 430/270, 281, 905, 915, 916, 917, 920, 283, 287, 288, 292; 204/159.18, 159.23

[56] References Cited

U.S. PATENT DOCUMENTS

| | | | |
|---|---|---|---|
| 3,445,234 | 5/1969 | Cescon et al. | 430/270 |
| 3,479,185 | 11/1969 | Cambers | 430/281 |
| 3,658,543 | 4/1972 | Gerlach | 430/270 |
| 3,661,461 | 5/1972 | Dessauer | 355/37 |
| 3,784,557 | 1/1974 | Cescon | 260/309 |

*Primary Examiner*—Jack P. Brammer

[57] ABSTRACT

Photoimaging compositions comprising (A) 2,4,5-triphenylimidazolyl dimer having selected substituents on the 2,4 and 5 phenyl rings and an extinction coefficient determined in methylene chloride at $10^{-5}$ to $10^{-3}$ mol/liter at 350 nm of at least 4000 liters/mol-cm and at 400 nm of at least 250 liters/mol-cm; and at least one of (B1) leuco dye or (B2) addition polymerizable ethylenically unsaturated monomeric compound. The new imaging compositions are useful in preparing dual response photoimaging products such as proofing papers, printout paper, overlay films and photopolymerizable elements. Improved imaging speed is achieved at equal concentration levels when compared with conventional 2,4,5-triphenylimidazolyl dimers.

16 Claims, No Drawings

DIMERS DERIVED FROM UNSYMMETRICAL 2,4,5,-TRIPHENYLIMIDAZOLE COMPOUNDS AS PHOTOINITIATORS

This is a division, of application Ser. No. 066,373 filed Aug. 14, 1979, now U.S. Pat. No. 4,252,887.

DESCRIPTION

1. Technical Field

This invention relates to photoimaging compositions. More particularly, it relates to photoimaging compositions containing selectively substituted 2,4,5-triphenylimidazolyl dimers.

2. Background Art

Photoimaging compositions utilizing hexaarylbiimidazole compounds in conjunction with either a leuco dye or an ethylenically unsaturated monomer compound, as well as other additives, are known. Such compositions are sensitive to radiation in the shorter wavelength range of the ultraviolet spectrum. For many reasons it is desirable that the spectral sensitivity of these compositions be extended into the longer wavelength range of the spectrum or the reactivity of these compositions be increased so that they can respond more efficiently to less costly lower energy light exposure sources. To accomplish this many additives have been used in conjunction with hexaarylbiimidazoles, e.g., aromatic hydrocarbons, coumarins, carbocyanine dyes, hydroxyphthalein dyes, acridine dyes, aminophenylketones, etc. The use of additives, while effective, is troublesome because not only does the presence of the specific additive increase the cost of the formulation, but it requires experimental work of skilled chemists to find additives of appropriate solubility characteristics and chemical properties to permit existence of the additive in the photoimaging composition, to develop the optimum formulations, and to maintain appropriate and effective quality control over the chosen additives. The known additives have been found to be effective in the formulations typical of hexaarylbiimidazole-containing photoimaging compositions. After a period of time, however, it has been found that there may be a tendency for crystallization to occur causing an undesired decrease in photosensitivity and a discontinuity in photo-response in the areas where the crystals form.

It is desirable that the above disadvantages be overcome and that formulations be prepared containing hexaphenylbiimidazole compounds sensitive to longer wavelengths of the spectrum and having increased radical reactivity.

DISCLOSURE OF THE INVENTION

In accordance with this invention there is provide a photoimaging composition comprising an admixture of (A) an 2,4,5-triphenylimidazolyl dimer of the formula:

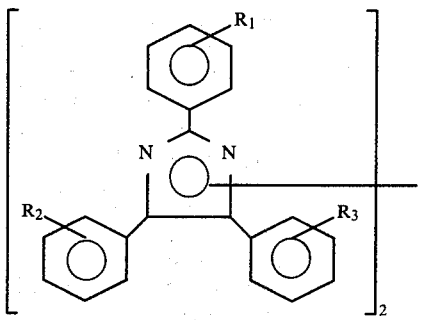

wherein $R_1$ is 2-bromo, 2-chloro, 2-fluoro, 2-alkyl of 1 to 4 carbon atoms and 2,4-dichloro;

$R_2$ is 2-bromo, 2-chloro, 2-fluoro, 4-chloro, 2-alkyl of 1 to 4 carbon atoms, 2-cyano, and 2-alkoxy wherein the alkyl radical is of 1 to 4 carbon atoms; and $R_3$ is 3,4-dimethoxy, 3,4-diethoxy, 2,3-dimethoxy, 2,4,6-trimethoxy, 4-alkoxy wherein the alkyl radical is of 1 to 4 carbon atoms and 3,4-methylenedioxy; the imidazolyl dimer having an extinction coefficient determined in methylene chloride at $10^{-5}$ to $10^{-3}$ mol/liter at 350 nm of at least 4000 liters/mol-cm and at 400 nm of at least 250 liters/mol-cm; and at least one compound taken from the group consisting of (B1) a leuco dye that is oxidizable to dye by the imidazolyl radicals; and (B2) an addition polymerizable ethylenically unsaturated monomeric compound.

The photoimaging compositions of the invention comprise the specific 2,4,5-triphenylimidazolyl dimers and either a dye in its leuco form, or, in the event that the composition is photopolymerizable, a compound having ethylenic unsaturation. Both the leuco dye and ethylenically unsaturated compound can be present in the composition as noted below. The photoimaging composition containing the specific 2,4,5-triphenylimidazolyl dimer and leuco dye is stabilized to prevent color build-up in the nonimage areas. The following processes have been found to be effective to achieve such stabilization: treatment with solution containing a free radical trap, e.g., hydroquinone, phenidone, etc.; inclusion in the coating of precursors of hydroquinone which lead to its generation by heat, e.g., dihydropyran adduct of ditertiarybutylhydroquinone; inclusion of quinones (photoactivatible oxidants) and hydrogen donor compounds (reductant components) which may be employed to generate hydroquinones by light exposure, preferably at wavelength distinct from the colorforming exposure; and photopolymerizable compounds which act as plasticizers to promote color formation until polymerized when they limit diffusion of color forming species and present formation of image color. It is desirable to add to the photoimaging composition a film-forming polymeric binder. Suitable inert solvents are generally present in preparing the formulations and plasticizers are commonly used therein. Additional components which can be present include: antiblocking agents, dyes, and white and colored pigments which do not act as sensitizers, etc.

In the photopolymerizable composition containing the specific 2,4,5-triphenylimidazolyl dimer and addition polymerizable ethylenically unsaturated compound there can be present a free radical producing, electron donor agent hydrogen donor (hydrogen donor), e.g., organic amines, mercaptans, certain halogen-containing compounds, active methylene compounds, etc. Optional components that can be present in the photopolymerizable composition are: film-forming polymeric binders, inert solvents, plasticizers, chain transfer agents, energy transfer dyes, oxygen scavengers, ultraviolet absorbers, etc. After imagewise exposure an image pattern can be observed in the photopolymerizable composition (in layer form) by toning with a colored toner or by solvent washout.

The specific 2,4,5-triphenylimidazolyl dimers useful in the photoimaging compositions are defined above. The dimers have what is classified as "infra-radical asymmetry". The selected triphenylimidazole precursor to the dimer is asymmetrical about a plane perpendicular to the plane of the triphenylimidazole molecule and bisecting the N-C-N bond angle of the formula set forth above.

This type of asymmetry is dependent on the substitution in the phenyl rings at the 4- and 5-positions on the imidazole ring. It is determined by the choice of the benzil precursor to the triphenylimidazole. Preferred compounds used in the compositions of this invention have been found to give rise to free radicals which, in the absence of leuco dyes, possess extended free radical life, i.e., show reduced tendency to recombine to give corresponding dimers. As dimerization removes reactive species, i.e., imidazolyl radicals, from the photoimaging compositions, reduced tendency to dimerize enhances imaging speed and performance. Examples 1 to 10 below illutrate the synthesis of the asymmetricl hexaphenylbiimidazoles of the invention wherein the selected benzoin and benzaldehyde are refluxed in methanol in the presence of copper acetate and ammonia, an adaptation of the procedure of Wiedenhagen et al., Ber. 70,570 (1937). Another preparation procedure involves heating a benzil and a benzaldehyde at 180° to 190° C. in formamide solution as disclosed in Belgian Pat. No. 589,417.

The specific triphenylimidazolyl dimers are present in 0.1 to 10.0 percent by weight of solids in the photoimaging compositions.

The leuco form of the dye which comprises one component of a photoimaging composition of the present invention is the reduced form of the dye having one or two hydrogen atoms, the removal of which together with an additional electron in certain cases produces the dye. Such dyes have been described, for example, in U.S. pat. No. 3,445,234, column 2, line 49 to column 8, line 55, incorporated by reference. The following classes are included:
(a) aminotriarylmethanes
(b) aminoxanthenes
(c) aminothioxanthenes
(d) amino-9,10-dihydroacridines
(e) aminophenoxazines
(f) aminophenothiazines
(g) aminodihydrophenazines
(h) aminodiphenylmethanes
(i) leuco indamines
(j) aminohydrocinnamic acids (cyanoethanes, leuco methines)
(k) hydrazines
(l) leuco indigoid dyes
(m) amino-2,3-dihydroanthraquinones
(n) tetrahalo-p,p'-biphenols
(o) 2(p-hydroxyphenyl)-4,5-diphenylimidazoles
(p) phenethylanilines Of these leuco forms, (a) through (i) form the dye by losing one hydrogen atom, while the leuco forms (j) through (p) lose two hydrogen atoms to produce the parent dye. Aminotriarylmethanes are preferred. A general preferred aminotriarylmethane class is that of the acid salts of aminotriarylmethanes wherein at least two of the aryl groups are phenyl groups having (a) an $R_1R_2N$-substituent in the position para to the bond to the methane carbon atom wherein $R_1$ and $R_2$ are each groups selected from hydrogen, $C_1$ to $C_{10}$ alkyl, 2-hydroxyethyl, 2-cyano-ethyl, or benzyl and (b) a group ortho to the methane carbon atom which is selected from lower alkyl (C is 1 to 4), lower alkoxy (C is 1 to 4), flourine, chlorine or bromine; and the third aryl group may be the same as or different from the first two, and when different is selected from (a) Phenyl which can be substituted with lower alkyl, lower alkoxy, chloro, diphenylamino, cyano, nitro, hydroxy, fluoro or bromo;

(b) Naphthyl which can be substituted with amino, di-lower alkylamino, alkylamino;

(c) Pyridyl which can be substituted with alkyl;

(d) Quinolyl;

(e) Indolinylidene which can be substituted with alkyl.

Preferably, $R_1$ and $R_2$ are hydrogen or alkyl of 1-4 carbon atoms. Leuco dye is present in 0.1 to 5.0 percent by weight of solids in the photoimaging composition.

With the leuco form of dyes which have amino or substituted amino groups within the dye structure and which are characterized as cationic dyes, an amine salt-forming mineral acid, organic acid, or an acid from a compound supplying acid is employed. The amount of acid usually varies from 0.33 mol to 1 mol per mol of amino nitrogen in the dye. The preferred quantity of acid is about 0.5 to 0.9 mol per mol of amino nitrogen. Representative acids which form the required amine salts are hydrochloric, hydrobromic, sulfuric, phosphoric, acetic, oxalic, p-toluenesulfonic, trichloroacetic, trifluoroacetic and perfluoroheptanoic acid. Other acids such as acids in the "Lewis" sense or acid sources which may be employed in the presence of water or moisture include zinc chloride, zinc bromide, and ferric chloride. Representative leuco dye salts include tris-(4-diethylamino-o-tolyl) methane zinc chloride, tris-(4-diethylamino-o-tolyl) methane oxalate, tris-(4-diethylamino-o-tolyl) methane p-toluene-sulfonate and the like.

The redox couple useful in the photoimaging composition is described in U.S. Pat. No. 3,658,543, column 9, lines 1 to 46, incorporated by reference. Preferred oxidants include 9,10-phenanthrenequinone alone or in admixture with 1,6- and 1,8-pyrenequinone which absorb principally in the 430 to 550 nm region. The reductant component of the redox couple is 100 to 10 percent of an acyl ester of triethanolamine of the formula:

where R is alkyl of 1 to 4 carbon atoms, and 0 to 90 percent of a $C_1$ to $C_4$ alkyl ester of nitrilotriacetic acid or of 3,3',3''-nitrilotripropionic acid. Triethanolamine triacetate and dibenzylethanolamine acetate are preferred reductant components. The molar ratios of oxidants to biimidazole used ranges from 0.01:1 to 2:1, preferably 0.2:1 to 0.6:1. The molar ratios of reductant to biimidazole used ranges from about 1:1 to about 90:1, preferably 10:1 to 20:1.

Optionally, other additives can be present in the photoimaging composition. Polymeric binders can be added to thicken the formulations or adhere them to substrates. The binders can also serve as a matrix for the color-forming composition. Light-transparent and film-forming polymers are preferred. Examples are ethyl cellulose, polyvinyl alcohol, polyvinyl chloride, polystyrene, polyvinyl acetate, poly-(methyl, propyl or butyl methacrylate), cellulose acetate, cellulose butyrate, cellulose acetate butyrate, cellulose nitrate, chlorinated rubber, copolymers of the above vinyl monomers, etc. The binder can be present in an amount from about 0.5 part to about 200 parts by weight per part of combined weight of the hexaphenylbiimidazole and leuco dye. Generally 5 to 20 parts by weight are used.

The binder composition can also contain inert infusible fillers such as titanium dioxide, organophilic colloidal silica, bentonite, powdered glass, micron-sized alumina and mica in minor, noninterfering amounts. Formulations containing micron-sized silicas, as, for example, the "Syloid" silica gels, sold by W. R. Grace & Co., are particularly useful for providing a "tooth" for pencil or ink receptivity and eliminating blocking tendencies.

With some polymers, it is desirable to add a plasticizer, e.g., solid or liquid, to give flexibility to the film or coating. Suitable plasticizers are disclosed in U.S. Pat. No. 3,658,543, column 10, lines 20 to 73, incorporated by reference. A preferred liquid plasticizer is Nonylphenoxypoly(ethyleneoxy)-ethanol. A preferred solid plasticizer is N-ethyl-p-toluenesulfonamide. The plasticizers can be used in concentration ranging from 1:20 to 5:3, preferably 1:5 to 1:2, based on the weight of polymeric binder used.

In preparing the formulation generally inert solvents are employed which are volatile at ordinary pressures. Examples include alcohols and ether alcohols such as methanol, ethanol, 1-propanol, 2-propanol, butanol, and ethylene glycol; esters such as methyl acetate and ethyl acetate; aromatics such as benzene, o-dichlorobenzene and toluene; ketones such as acetone, methyl ethyl ketone and 3-pentanone; aliphatic halocarbons such as methylene chloride, chloroform, 1,1,2-trichloroethane. 1,1,2,2-tetrachloroethane and 1,1,2-trichloroethylene; miscellaneous solvents such as dimethylsulfoxide, pyridine, tetrahydrofuran, dioxane, dicyanocyclobutane and 1-methyl-2-oxo-hexamethyleneimine; and mixtures of these solvents in various proportions as may be required to attain solutions. It is often beneficial to leave a small residue of solvent in the dried composition so that the desired degree of imaging can be obtained upon subsequent irradiation.

Useful optional antiblocking agents present to prevent the coatings from adhering to one another include

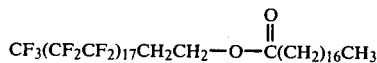

and other known agents.

In the photopolymerizable embodiment of this invention, in addition to the hexaphenylbiimidazole compounds described above, at least one addition polymerizable ethylenically unsaturated compound having at least one polymerizable ethylenic group is present. Such compounds are capable of forming a high polymer by free-radical initiated, chain-propagating, addition polymerization. Preferably, the monomeric compound has at least two terminal ethylenically unsaturated groups, e.g., 2 to 4 groups. The monomeric compounds are nongaseous, i.e., at 20° C. and atmospheric pressure, have a normal boiling point about 100° C. and a plasticizing action on any thermoplastic polymeric binder that may be present.

Ethylenically unsaturated monomeric compounds useful in this invention include monomeric compounds or polymers wherein the ethylenic unsaturation is present as an extralinear substituent attached to the polymer backbone. Useful monomeric compounds are: alkylene or a polyalkylene glycol diacrylate prepared from an alkylene glycol or 2 to 15 carbons or a polyalkylene ether glycol of 1 to 10 ether linkages; unsaturated esters of alcohols, preferably polyols and particularly such esters of the alphamethylene carboxylic acids, e.g., ethylene glycol diacrylate, diethylene glycol diacrylate, glycerol diacrylate, glycerol triacrylate, ethylene glycol dimethacrylate, 1,3-propanediol dimethacrylate, 1,2,4-butanetriol trimethacrylate, 1,4-cyclohexanediol diacrylate, 1,4-benzenediol dimethacrylate, pentaerythritol tetramethacrylate, 1,3-propanediol diacrylate, 1,5-pentanediol dimethacrylate, pentaerythritol triacrylate; the bis-acrylate and methacrylates of polyethylene glycols of molecular weight 200-500, etc.; unsaturated amides, particularly those of the alpha-methylene carboxylic acids, and especially those of alpha-omega-diamines and oxygen-interrupted omega-diamines, such as methylene bis-acrylamide, methylene bis-methacrylamide, ethylene bis-methacrylamide, 1,6-hexamethylene bis-acrylamide, diethylene triamine trismethacrylamide, bis(gamma-methacrylamidopropoxy) ethane, beta methacrylamidoethyl methacrylate, N-(betahydroxyethyl)-beta-(methacrylamido) ethyl acrylate and N,N-bis (beta-methacryloxyethyl) acrylamide; vinyl esters such as divinyl succinate, divinyl adipate, divinyl phthalate, divinyl terephthalate; divinyl benzene-1,4-disulfonate, and divinyl butane-1,4-disulfonate, styrene and derivatives thereof and unsaturated aldehyde, such as sorbaldehyde (hexadienal).

Useful polymers having ethylenically unsaturated groups attached thereto are: the polymerizable, ethylenically unsaturated polymers of U.S. Pat. No. 3,043,805 and U.S. Pat. No. 2,929,710, e.g., polyvinyl acetate/acrylate, cellulose acetate/acrylate, cellulose, acetate/methacrylate, N-acrylyloxymethyl polyamide, etc.; polyoxyethylated trimethylol propane triacrylate, polytetramethylene glycol diacrylate, etc., disclosed in U.S. Pat. No. 3,418,295.

Suitable thermal polymerization inhibitors that can be used in photopolymerizable compositions include p-methoxyphenol, hydroquinone, and alkyl- and aryl-substituted hydroquinones and quinones, tert-butyl catechol, pyrogallol, copper resinate, naphthylamines, beta-naphthol, cuprous chloride, 2,6-di-tert-butyl-p-cresol, phenothiazine, pyridine, nitrobenzene and dinitrobenzene. Other useful inhibitors, include p-toluquinone and chloranil, and thiazine dyes, e.g., Thionine Blude G (C.I. Basic Blue 25), and Toluidine Blue O (C.I. Basic Blue 17). In certain embodiments of the invention containing certain dye photoinitiators, however, no thermal inhibitor is required since these initiators have a dual function and in the dark serve as thermal inhibitors.

Free radical producing, electron donor agents (hydrogen donor) and active methylene compounds that can be present in the photopolymerizable photoimaging composition are described in U.S. Pat. No. 3,479,185, column 2, line 50 to column 3, line 3, incorporated by reference. The electron donor agent has a reactive atom, usually hydrogen, which is removable and in the presence of the radical of the substituted 2,4,5-triphenylimidazolyl dimer yields a radical which reacts with the monomeric compound to initiate growth of polymer chains.

Examples of preferred electron or hydrogen donor compounds include compounds that form a stable composition with the hexaphenylbiimidazole compound in the dark. The agent can be an amine, e.g., a tertiary amine. The amine-substituted leuco dyes are useful, especially those having at least one dialkylamino group. Also, any leuco triphenylamine dye or various salts of the dye, e.g., the HCl salt of the leuco blue dye can be used. Illustrations of suitable dyes include tris-(4-N,N-diethylamino-o-tolyl)-methane trihydrochloride, bis(4-N,N-diethylamino-o-tolyl)triphenylmethane, bis(4-N,N-diethylamino-tolyl) methylenedioxyphenylmethane, leuco neutral shade dye, i.e., bis(4-N,N-diethylamino-o-tolyl)-benzyl thiophenylmethane, Leuco Malachite Green (C.I. Basic Green 4), leuco forms of Crystal Violet, Brilliant Green (C.I. Basic Green 1), Victorial Green 3B (C.I. Basic Green 4), Acid Green GG (C.I. Acid Green 3), Methyl Violet (C.I. Basic Violet 1), Rosaniline (C.I. Basic Violet 14), etc. The salt forms, e.g., HCl salt, salts with Lewis acid, sulfuric acid salts, p-toluene sulfonic acid salts, etc., of the leuco dye is preferred for use.

Additional suitable, electron donor agents which can be used singly or in combination include aniline, N-methylaniline, N,N-diethylaniline, N,N-diethylcresidine, triethanolamine, ascorbic acid, 2-allylthiourea, sarcosin, N,N-diethylglycine, trihexylamine, diethylcyclohexylamine, N,N,N',N'-tetramethylethylenediamine, diethylaminoethanol, ethylaminoethanol, N,N,N',N'-ethylenediaminotetracetic acid, N-methylpyrrolidone, N,N,N',N'',N''-pentamethyldiethylenetriamine, N,N-diethylxylidene, N,N'-dimethyl-1,4-piperazine, N-$\beta$-hydroxyethylpiperidine, N-ethylmorpholine, and related amino compounds. While the tertiary amines and especially the aromatic tertiary amines having at least one $CH_2$ group adjacent to the nitrogen atoms are preferred, a combination of two radical generating agents such as a tertiary amine, e.g., N,N-dimethylaniline, and a secondary amine, e.g., N-phenylglycine, appear especially useful.

In a photoimaging composition containing the hexaphenylbiimidazole, monomeric compound and electron donor agent, the light-sensitivity, speed, or degree of polymerization is dependent on the concentratic of the hexaphenylbiimidazole and electron donor agent. Useful compositions may be limited in part by the solubilities of the components. It was discovered that the speed increased up to a certain concentration of hexaphenylbiimidazole and electron donor agent, and an increase of the concentration past that level did not produce any increase in speed and in some instances the speed dropped. When a leuco dye was used as the electron donor agent, a mole ratio of leuco dye to the hexaphenylbiimidazole of 1.0 to 1.4 gave the best results as to photospeed and stability.

As indicated above, optionally, but preferably, a polymeric binder can be present in the photopolymerizable photoimaging system. Suitable binders include: the polymerized methylmethacrylate resins including copolymers thereof, polyvinyl acetals such as polyvinyl butyral and polyvinyl formal, vinylidene chloride copolymers (e.g., vinylidene chloride/acrylonitrile, vinylidene chloride/methacrylate and vinylidene chloride/vinylacetate copolymers), synthetic rubbers (e.g, butadiene/acrylonitrile copolymers and chloro-2-butadine-1,3-polymers, cellulose esters (e.g, cellulose acetate, cellulose acetate succinate and cellulose acetate butyrate), polyvinyl esters (e.g, polyvinyl acetate/acrylate, polyvinyl acetate/methacrylate and polyvinyl acetate), polyvinyl chloride and copolymers (e.g, polyvinyl chloride/acetate), polyurethanes, polystyrene and the polymeric binders described in U.S. Pat. No. 3,418,295. The monomeric compound and polymeric binder are present in the photoimaging composition in from 3 to 97 to 3 parts by weight, respectively. 0.001 to 2.0 parts by weight per 100 parts by weight of monomer and binder of a thermal addition polymerization inhibitor preferably is present.

Solvents, plasticizers, e.g., 10 to 50 percent by weight based on the weight of monomer, antiblocking agents, ultraviolet absorbers as described in the Examples, e.g., Example 18, can be present in the photopolymerizable photoimaging composition. In addition, oxygen scavengers, e.g., 2-allyl thiourea, dimethylsulfoxide, stannous chloride, N-phenylglycine, etc., can be present. The oxygen scavenger appears to eliminate or reduce the induction period usually found in a photopolymerization reaction, possibly by consumption of oxygen in the layer prior to exposure.

Another additive that can be present in the photopolymerizable composition is a chain transfer agent, in an amount of from 0.01 to 0.1 mol/mol electron donor agent such as a leuco dye, e.g., N-phenylglycine, 1,1-dimethyl-3,5-diketocyclohexane, or organic thiols, e.g., 2-mercaptobenzothiazole, 2-mercaptobenzoxazole, 2-mercaptobenzimidazole, pentaerythritol tetrakis (mercaptoacetate), 4-acetamidothiophenol, mercaptosuccinic acid, dodecanethiol, beta-mercaptoethanol, beta-mercaptoethanol, or other organic thiol.

Still another additive is an energy-transfer dye of the type disclosed in U.S. Pat. No. 3,479,185, column 5, lines 57 to 74, incorporated by reference. Generally such energy-transfer dyes are present in 0.5 to 3.0% by weight based on the weight of monomer or binder component, if present.

For imaging uses, the compositions of this invention may be coated upon or impregnated in substrates following known techniques. Substrates include materials commonly used in the graphic arts and in decorative applications such as paper ranging from tissue paper to heavy cardboard, films of plastics and polymeric materials such as regenerated cellulose, cellulose acetate, cellulose nitrate, polyethylene terephthalate, vinyl polymers and copolymers, polyethylene, polyvinyl-acetate, polymethyl methacrylate, polyvinylchloride; textile fabrics; glass, wood and metals. The composition, usually as a solution in a carrier solvent described above, may be sprayed, brushed, applied by a roller or an immersion coater, flowed over the surface, picked up by immersion or spread by other means, and the solvent evaporated.

Any convenient source providing radiation of wavelengths in the range of 200 nm to 420 nm can be used to activate the photoimaging composition for triphenylimidazolyl radical formation, image formation, and photopolymerization initiation. The radiation may be natural or artificial, monochromatic or polychromatic, incoherent or coherent, and should be sufficiently intense to activate a substantial proportion of the photoinitiator.

Conventional light sources include fluorescent lamps, mercury, metal additive and arc lamps. Coherent light sources are the pulsed nitrogen-, xenon, argon ion- and ionized neon-lasers whose emissions fall within or overlap the ultraviolet or visible absorption bands of the photoinitiator. Ultraviolet and near-visible radiation-emitting cathode ray tubes widely useful in printout systems for writing on photosensitive materials are also useful with the subject compositions.

Images may be formed by writing with a beam of the activating light or by exposing to such light a selected area behind a negative, stencil, or other relatively opaque pattern. The negative may be silver on cellulose acetate or polyester film or one in which its opacity results from aggregations of areas having different refractive indices. Image formation may also be effected in conventional diazo printing apparatus, graphic arts exposure or electronic flash equipment and by projection as described in U.S. Pat. No. 3,661,461. The light exposure time may vary from a fraction of a second to several minutes, depending upon the intensity and spectral energy distribution of the light, its distance from the composition, the nature and amount of the composition available, and the intensity of color in the image desired.

BEST MODE FOR CARRYING OUT THE INVENTION

The best mode is illustrated in Example 1 wherein the hexaarylbiimidazole compound is 2,2′,4,4′-tetrakis(o-chlorophenyl)-5,5′-bis(m,p-dimethoxyphenyl)-biimidazole.

INDUSTRIAL APPLICABILITY

The hexaphenylbiimidazoles are useful as photoinitiators in various photoimaging formulations which can be used in the manufacture of dual response photoimaging products, where controlled sequential exposure with ultraviolet and visible light may yield negative to positive images, e.g., Dylux ® proofing papers, printout paper, e.g., for the Du Pont "aca" automatic clinical analyzer; garment pattern papers, overlay films, heatfix type papers and films; and in photopolymerizable layers and elements useful for printing purposes as well as a variety of copying, i.e., office copying, recording, decorative, and photoresist applications. The formulations containing the hexaarylbiimidazoles have improved absorption in the imaging areas of 345 to 400 nm and form imidazolyl radicals with increased radical life which permits their more effective utilization at lower concentration levels. The black formulation may be imaged with a variety of exposure sources, e.g., black light blue, black light, xenon, mercury vapor, etc. without use of a filter due to extended absorption. The stability of the formulations is improved. It is possible to fix the formulations faster because a lower amount of hexaphenylbiimidazole compound is present and must subsequently be destroyed during fixing. The imaging speed is also improved at equal concentration levels with current photoinitiators. Cost of the formulations is reduced because of the lower cost of ingredients for manufacture of the biimidazole as well as the fact that lower concentrations can be used.

EXAMPLES

The following examples illustrate the invention wherein the percentages are by weight.

EXAMPLES 1 TO 10

Synthesis of Hexaphenylbiimidazoles

The asymmetrical hexaphenylbiimidazoles of this invention are prepared according to the following procedures.

A. Benzoin Condensation

To a one-liter flask equipped with a stirrer, reflux condenser and nitrogen inlet tube is charged:

| Ingredient | Amount (g) |
| --- | --- |
| 3,4-Dimethoxybenzaldehyde | 200 (1,20 mols) |
| 2-Chlorobenzaldehyde | 174 (1.24 mols) |
| Methanol | 225 ml |
| Water | 65 ml |
| Potassium Cyanide | 10 |

The system is purged with nitrogen, and the reaction mixture is refluxed for 45 minutes. The flask is cooled in an ice bath to induce crystallization which is followed by an additional 4.25 hours refluxing and cooling to room temperature with stirring. The precipitated benzoin is filtered off, is washed with a 175 ml methanol/25 ml water mixture, followed by a 1000 ml of water wash and is then recrystallized from ethanol. Table 1 summarizes the results of the benzoin preparation. Except for the indicated variations in the molar scale of the reactions, the procedure described above was followed with appropriate modification of the amounts of reactants.

TABLE 1

Benzoins R—CO—CH(OH)R$_1$

| R aldehyde | R$_1$ Aldehyde | Reaction Scale (Molar) | M.P. (°C.) | Yield (%) |
| --- | --- | --- | --- | --- |
| 3,4-dimethoxy | 2-chloro | 1.2 | 116–118 | 69 |
| 3,4-dimethoxy | 2-bromo | 0.2 | 122–124 | 58 |
| 3,4-dimethoxy | 2-methyl | 1.0 | 118–19 | 23[1] |
| 4-ethoxy | 2-chloro | 1.2 | 123–5 | 74 |
| 3,4-dimethoxy | 4-chloro | 1.2 | 100–2 | 21[2] |
| 3,4-dimethoxy | 2-fluoro | 0.9 | 124–6 | 52 |
| 3,4-methyleneoxy | 2-chloro | 1.2 | 115–6 | 63 |

[1]Oil from reaction; crystals obtained from ether extraction.
[2]Oil from reaction; crystals obtained from ethanol/petroleum ether.

B. Benzil Synthesis

To a 3-liter flask fitted with a stirrer, reflux condenser and thermometer, is added Mixture 1 which contains the following ingredients in the amounts indicated:

| Ingredient | Amount (g) |
| --- | --- |
| Cupric acetate | 2.18 |
| Water | 121.0 |
| Acetic acid | 303.0 |
| Ammonium nitrate | 112.0 |

Mixture 1 is heated to aout 95° C. to obtain a solution. Mixture 2 is prepared from the following ingredients in the amounts indicated:

| Mixture 2 | |
|---|---|
| Ingredient | Amount (g) |
| 3,4-Dimethoxy-2'-chlorobenzoin | 303.0 |
| Acetic acid | 909.0 |

Mixture 2 is heated to 70°–80° C. to maintain solution and is added portionwise to Mixture 1 in the flask as follows:

Portion 1: about 10% (~120 g) of Mixture 2 to start the reaction; nitrogen evolution is observed in 1 to 3 minutes.

Portion 2: About 40% (~450 g) of Mixture 2; the reaction temperature is maintained at 95° to 105° C.

Portion 3: Balance of Mixture 2 (~600 g) 1 to 2 hours after addition of Portion 2; the temperature of the mixture is held at 105° C. for an additional hour.

Following an additional five-hour reflux period to complete the reaction, the mixture is allowed to cool overnight to room conditions. The mixture is chilled to 5° to 10° C. with stirring and is filtered twice, first with a water (80 g)/acetone (320 g) solution chilled to 5° to 10° C., and then with 2000 ml of water. The filter cake is held for the preparation of the hexaphenyl-biimidazoles. Table 2 summarizes the results of benzil preparation.

TABLE 2

Benzils $R_2-\overset{O}{\overset{\|}{C}}-\overset{O}{\overset{\|}{C}}-R_3$

| $R_2$ | $R_3$ | M.P.(°C.) |
|---|---|---|
| 3,4-dimethoxy | 2-Cl | |
| 3,4-dimethoxy | 2-Br | 122–124 |
| 3,4-dimethoxy | 2-methyl | 124–126 |
| 4-ethoxy | 2-Cl | 90–91 |
| 3,4-dimethoxy | 4-Cl | 135–136 |
| 3,4-dimethoxy | 2-F | 96–98 |
| 3,4-methylene-oxy | 2-Cl | 91–92 |

C. Imidazole Synthesis

To a 500 ml flask equipped with a stirrer, reflux condenser and nitrogen inlet tube is charged:

| Ingredient | Amount (g) |
|---|---|
| Benzil Compound | (See Table 3 below) (0.133 mol) |
| Benzaldehyde compound | (See Table 3 below) (0.146 mol) |
| Ammonium acetate | 45 |
| Glacial acetic acid | 120 ml |

The reaction mixture is swept with nitrogen and refluxed for 12 hours and allowed to cool to room temperature overnight. The reaction mixture is then poured into 2 liters of distilled water containing 7 g of potassium bisulfite to complex the unreacted aldehyde. A white solid precipitates which is filtered, washed with 2000 ml water, and dried. N.M.R. analysis shows that the acetate salt of the imidazole formed. No attempt is made to prepare the free base because in the final step of the synthesis the oxidative dimerization is carried out in strong base and the acetate salt is converted to the base at that stage.

TABLE 3

| Compound No. | Benzil Compound | Amount (g) |
|---|---|---|
| 1. | 3,4-Dimethoxy-2'-chlorobenzil | 40.6 |
| 2. | 3,4-Dimethoxy-2'-fluorobenzil | 38.3 |
| 3. | 4-Ethoxy-2'-chlorobenzil | 38.3 |
| 4. | 3,4-Dimethoxy-2'-chlorobenzil | 40.6 |
| 5. | 3,4-Methylenedioxy-2'-chlorobenzil | 33.8 |
| 6. | 3,4-Dimethoxy-4'-chlorobenzil | 40.6 |
| 7. | 3,4-Dimethoxy-2'-chlorobenzil | 40.6 |
| 8. | 3,4-Dimethoxy-2'-chlorobenzil | 40.6 |
| 9. | 3,4-Dimethoxy-2'-methylbenzil | 37.8 |
| 10. | 3,4-Dimethoxy-2'-bromobenzil | 46.4 |

TABLE 4

| Compound No. | Benzaldehyde Compound | Amount (g) |
|---|---|---|
| 1. | 2-Chlorobenzaldehyde | 20.5 |
| 2. | 2-Chlorobenzaldehyde | 20.6 |
| 3. | 2-Chlorobenzaldehyde | 20.6 |
| 4. | 2-Bromobenzaldehyde | 27.0 |
| 5. | 2-Chlorobenzaldehyde | 20.6 |
| 6. | 2-Chlorobenzaldehyde | 20.6 |
| 7. | 2-Methylbenzaldehyde | 17.5 |
| 8. | 2,4-Dichlorobenzaldehyde | 25.4 |
| 9. | 2-Chlorobenzaldehyde | 20.6 |
| 10. | 2-Chlorobenzaldehyde | 20.6 |

Table 5 summarizes the results of triphenylimidazole preparation.

TABLE 5

| | A | A' | B | C | D | D' |
|---|---|---|---|---|---|---|
| 1. | Cl | — | OCH$_3$ | OCH$_3$ | Cl | — |
| 2. | Cl | — | OCH$_3$ | OCH$_3$ | F | — |
| 3. | Cl | — | — | OEt | Cl | — |
| 4. | Br | — | OCH$_3$ | OCH$_3$ | Cl | — |
| 5. | Cl | — | O—CH$_2$—O* | — | Cl | — |
| 6. | Cl | — | OCH$_3$ | OCH$_3$ | — | Cl |
| 7. | CH$_3$ | — | OCH$_3$ | OCH$_3$ | Cl | — |
| 8. | Cl | Cl | OCH$_3$ | OCH$_3$ | Cl | — |
| 9. | Cl | — | OCH$_3$ | OCH$_3$ | CH$_3$ | — |
| 10. | Cl | — | OCH$_3$ | OCH$_3$ | Br | — |

*derived form piperonal

The dimers of the triphenylimidazolyl radicals derived from each of the specific triphenylimidazoles shown in Table 5 above are prepared by the following procedure. Into a 250 ml flask equipped with stirrer and condensor is placed one of the ten triphenylimidazoles in the amount indicated:

| Ingredient | Amount (g) |
|---|---|
| Triphenylimidazole (0.0471 mol) | |
| 1. | 20.0 |
| 2. | 19.2 |
| 3. | 19.2 |
| 4. | 22.1 |
| 5. | 19.2 |
| 6. | 20.0 |
| 7. | 19.0 |
| 8. | 21.7 |
| 9. | 19.0 |
| 10. | 22.1 |
| Methylene chloride | 125.0 ml |
| $K_3Fe(CN)_6$ | 20.7 |
| Water | 65.0 ml |
| Sodium hydroxide (50%) | 20.0 |

After refluxing for about 18 hours and cooling, 100 ml of water is added. The methylene chloride layer is separated and the aqueous phase is extracted with 50 ml of methylene chloride. The combined methylene chloride layers are washed twice with 70 ml water and are dried over anhydrous sodium sulphate. The methylene chloride is evaporated carefully to determine the yield and methylene chloride is added to make a 15% solution.

TABLE 6

| Dimer No. and Rank[a] | Conversion (%) | Molar Extinction Coefficient* | | Density (Trans.) Speed | | |
|---|---|---|---|---|---|---|
| | | 350 nm[b] | 400 nm[c] | Dmax | Step | Dmin |
| 1. | 88 | 5763 | 1451 | 0.73 | 0.59 | 0.30 |
| 2. | 58 | 4633 | 506 | 0.68 | 0.56 | 0.26 |
| 3. | 65 | 4672 | 253 | 0.65 | 0.45 | 0.22 |
| 4. | 89 | 4941 | 588 | 0.57 | 0.41 | 0.19 |
| 5. | 54 | 5848 | 1089 | 0.60 | 0.39 | 0.17 |
| 6. | 85 | 4364 | 844 | 0.81 | 0.48 | 0.2 |
| 7. | 96 | 5338 | 1128 | 0.46 | 0.41 | 0.19 |
| 8. | 79 | 4598 | 1150 | — | 0.45 | 0.24 |
| 9. | 88 | 5338 | 502 | 0.60 | 0.45 | 0.29 |
| 10. | 70 | 4706 | 971 | 0.78 | 0.52 | 0.28 |

*Molar Extinction Coefficient is determined in methylene chloride at $10^{-5}$ to $10^{-3}$ mol/liter, the values being expressed in liters/mol-cm.
[a]Visual comparison of sensitometric strips, lowest number is fastest. Dimers derived from triphenylimidazoles Table 5.
[b]Extinction coefficient for Control 2, Example 11 is 410 and Control 1, Example 11 is 2550.
[c]Extinction coefficient for Controls 1 and 2, Example 11 are <200.

The above ten triphenylbiimidazolyl dimers are used as new photoinitiators in photosensitive compositions containing the following ingredients in the amounts indicated:

| Ingredient | Amount (weight %) |
|---|---|
| Acetone (solvent) | 72.000 |
| Isopropanol (solvent) | 8.000 |
| Dodecylbenzenesulfonic acid (proton acid) | 0.727 |
| Tris(p-diethylamino-o-tolyl)methane (leuco cyan dye) | 0.275 |
| N-Ethyl-p-toluenesulfonamide (solid plasticizer) | 2.890 |
| o-Phenylphenol condensate with average of ~2.25 mols ethyleneoxide (plasticizer) | 2.385 |
| Triphenylimidazolyl dimer (photoinitiator)* (one of compounds 1 to 10, Table 6) | 0.434 |
| Mixture of ~83% 1,6- and ~17% 1,8-pyrenequinones (oxidant) | 0.004 |
| 9,10-Phenanthrenequinone (oxidant) | 0.139 |
| Triethanolamine triacetate (hydrogen donor) | 2.013 |
| $CF_3(CF_2CF_2)_{17}CH_2CH_2-O-\overset{O}{\underset{\parallel}{C}}-(CH_2)_{16}CH_3$ (anti-blocking agent) | 0.020 |
| Silica gel of 9µ average particle diameter surface area of 675 meters squared per gram, bulk density ~465 kg/m³ (anti-blocking agent) | 0.606 |
| Cellulose acetate butyrate (~27% butyryl) content, ~1 hydroxyl/2 anydroglucose units, and a viscosity of 56–131 poises by ASTM D-817-65-D (binder) | 10.507 |
| Total | 100.000 |

*added as a 15% solution by weight in methylene chloride (2.2 ml)

The photosensitive compositions are coated with a 0.004 inch (~100 nm) doctor blade on Schweitzer 32-HG paper and are dried at normal room conditions. The dry coatings are imaged by exposure through an image-bearing transparency for 30 seconds to 2.75 microwatts/cm² of black light blue radiation and are deactivated by exposure to room light to remove yellow background and render coatings insensitive to further ultraviolet irradiation. All the compositions provide good colored images with low background density.

EXAMPLE 11

Three coating lacquers are prepared as follows:

| Ingredient | Amount (g) |
|---|---|
| Acetone | 184.0 |
| Cellulose acetate butyrate ~27% butyryl content hydroxyl/2 anhydroglucose units and viscosity is 7.5–15 poises by ASTM D-817-65-D | 24.0 |
| o-Phenylphenol condensed with average of ~2.25 mols ethylene oxide | 16.0 |
| [Tris-(2-methyl-4-diethylaminophenyl)-methane] | 1.2 |
| p-Toluenesulfonic acid | 1.4 |
| 7-Diethylamino-4-methylcoumarin | 0.4 |

To each of three 11.4 g aliquots of the above lacquers is added $1.6 \times 10^{-4}$ mol of one of the following hexaphenylbiimidazole compounds:
1. 2,2'-bis(o-chlorophenyl)-4,4',5,5'-tetrakis(m-methoxyphenyl)-biimidazole (Control 1)
2. 2,2'-bis(o-chlorophenyl)-4,4',5,5'-tetraphenyl-biimidazole (Control 2)
3. 2,2',4,4'-tetrakis(o-chlorophenyl)-5,5'-bis(m,p-dimethoxyphenyl)-biimidazole.

Films are cast with a 040 coating bar on Schweitzer 32-HG paper and are dried at normal room conditions. Portions of the films are exposed as indicated in Table 7. The reflectance densities are measured with a MacBeth Quantalog reflectance densitometer.

TABLE 7

| Exposure Source | Time(sec) | Reflectance Densities Coatings | | |
|---|---|---|---|---|
| | | 1 | 2 | 3 |
| 1. None | | 0.08 | 0.04 | 0.09 |
| 2. Black light blue (365 nm peak) | 60 | 1.46 | 1.53 | 1.65 |
| 3. Vivitar 292 Photoflash | | | | |

TABLE 7-continued

| Exposure Source | Time(sec) | Reflectance Densities Coatings | | |
|---|---|---|---|---|
| | | 1 | 2 | 3 |
| 6000° K. no filter | 0.001 | 1.52 | 1.52 | 1.55 |
| 4. Same as source 3 but use 0-51 filter[a] | 0.001 | 1.08 | 1.03 | 1.25 |
| 5. Same as source 3 but use 3-75 filter[b] | 0.001 | 0.99 | 0.99 | 1.10 |
| 6. Same as source 3 but use 3-74 filter[c] | 0.001 | 0.66 | 0.44 | 0.69 |
| 7. Same as source 3 but use 3-72 filter[d] | 0.001 | 0.24 | 0.18 | 0.45 |

[a] less than 0.5% transmission at less than 334 nm; greater than 65% transmission at greater than 405 nm
[b] less than 0.5% transmission at less than 373 nm; greater than 65% transmission at greater than 427 nm
[c] less than 0.5% transmission at less than 403 nm; greater than 65% transmission at greater than 436 nm
[d] less than 0.5% transmission at less than 444 nm; greater than 65% transmission at greater than 466 nm This example illustrates that the hexaphenylbiimidazole compound of the invention present in coating 3 has greater absorption of actinic radiation at longer wavelengths as compared to the two control hexaphenylbiimidazole compounds present in coatings 1 and 2.

Examples 12 to 13 which follow illustrate various uses for the preferred hexaphenylbiimidazole compound, 2,2',4,4'-tetrakis(o-chlorophenyl)-5,5'-bis(m,p-dimethoxyphenyl)-biimidazole.

EXAMPLE 12

This example illustrates a magenta color-forming system.

A coating solution is prepared by mixing the following ingredients in the amounts indicated:

| Ingredient | Amount (g) |
|---|---|
| Methylene chloride | 295.0 |
| Isopropanol | 21.0 |
| Cellulose acetate butyrate described in Example 11 | 42.2 |
| Triethanolamine triacetate | 0.01 |
| 1-Phenylpyrazolidine-3-one | 0.106 |
| p-Toluenesulfonic acid | 0.347 |
| N-Ethyl-p-toluenesulfonamide | 3.93 |
| Nonylphenoxypoly(etheneoxy)-ethanol, nonionic surfactant and plasticizer | 3.93 |
| 7-Diethylamino-4-methylcoumarin | 1.0 |
| Hexaphenylbiimidazole No. 3, Example 11 | 4.64 |

The solution is coated on 0.003 inch (0.076 mm) thick polyethylene terephthalate film with a 025 coating bar and is allowed to dry. A 10-second exposure to ultraviolet radiation from BLB lamps gives a magenta image reflectance density of 0.64 when read over a white paper surface. A 20-second exposure to visible light with SDZ fluorescent lamps, gives an optical density of 1.06. The coating is deactivated by passing it through a solution containing 235 g water, 115 g isopropanol, 3.5 g sodium sulfite, 3.5 g acetic acid and 7.0 g 1-pheylpyrazolidine-3-one.

EXAMPLE 13

This example illustrates a negative-working garment pattern paper.

A coating solution is prepared by mixing the following ingredients in the amounts indicated:

| Ingredient | Amount (g) |
|---|---|
| Methylene chloride | 385.0 |
| Isopropanol | 70.0 |
| Cellulose acetate butyrate as in Example 11 except that the viscosity is 56–131 poises by ASTM D-817-65-D | 38.0 |
| Nonylphenoxypoly(etheneoxy)-ethanol | 28.0 |
| p-Toluenesulfonic acid | 2.74 |
| Silica gel of 9.0μ average particle diameter, 675 m²/gm surface area, bulk density ~465 Kg/m³ | 2.90 |
| Mixture of ~83% 1,6- and ~17% 1,8-pyrenequinones | 0.047 |
| Phenanthrenequinone | 0.141 |
| $CF_3(CF_2CF_2)_{17}CH_2CH_2-O-C(CH_2)_{16}CH_3$ (with =O on central C) | 0.30 |
| 7-Diethylamino-4-methylcoumarin | 0.46 |
| 3,4-Dimethoxyphenyl-bis(4-diethylamine-2-methylphenyl) methane | 0.38 |
| Rhodamine 5 GLD (C.I. 45160) | 0.18 |
| Hexaphenylbiimidazole No. 3, Example 11 | 0.57 |

The solution is coated on Schweitzer Sub 14 paper with a 010 coating bar to give a coating weight of ~4.0 mg/dm². After exposure to an ultraviolet radiation source for 60 seconds, an optical density of 0.7 is obtained.

EXAMPLE 14

This example illustrates the preparation of proofpaper, A yields cyan and B yields black images.

A coating lacquer is prepared by mixing the following ingredients in the amounts indicated:

| Coating A | |
|---|---|
| Ingredient | Amount (g) |
| Methylene chloride | 37.1 |
| Isopropanol | 4.1 |
| Cellulose acetate butyrate described in Example 13 | 5.2 |
| Pyrenequinone as described in Example 13 | 0.0031 |
| Phenanthrequinone | 0.050 |
| $CF_3(CF_2CF_2)_{17}CH_2CH_2-O-C(CH_2)_{16}CH_3$ (with =O on central C) | 0.044 |
| 7-Diethylamino-4-methylcoumarin | 0.078 |
| Dodecylbenzenesulfonic acid | 0.435 |
| Triethanolamine triacetate | 0.96 |
| o-Phenylphenol condensed with average of ~2.25 mols ethylene oxide | 1.0 |
| Silica gel described in Example 13 | 0.35 |
| Hexaphenylbiimidazole No. 3, Example 11 | 0.152 |

The solution is coated on Schweitzer 32-HG paper with a 020 bar, and the dried coating is exposed for 60 seconds to ultraviolet radiation (BLB lamps) through a lithographic negative. An image density of 1.0 is read on a MacBeth Quantalog Reflectance densitometer. The coating can also be exposed in a positive manner, with the initial light source a bank of SDZ fluorescent lamps, through a lithographic negative, followed by a flooding exposure with BLB lamps. An image with density of 1.0, and background of 0.1 is attained.

A similar coating solution as described above, but containing 0.18 g of the hexaphenylbiimidazole instead of 0.152 g, results in increased contrast; 60 seconds exposure to ultraviolet radiation gives an optical density of 1.3, with background of 0.15, after 1 hour ambient light exposure.

The concentration of the hexaphenylbiimidazole is reduced further to 0.12 g in the above coating lacquer. A reduced optical density of 0.7 with background of 0.11 is obtained, after a 60-second exposure to ultraviolet radiation and a 1 hour ambient light exposure.

A coating lacquer in which 2,2'-bis(o-chlorophenyl)-4,4',5,5'-tetrakis-(m-methoxyphenyl)biimidazole is employed instead of the hexaphenylbiimidazole No. 3 as described above, requires 0.36 g to achieve an optical density of 1.05, with background of 0.1 and 0.61 g for an image density of 1.1. At the higher concentration, it is not possible to obtain a low background in a positive exposure mode, as a color buildup of 0.41 is observed. A lower background is observed, however, when samples are exposed in ambient light for an hour.

A coating lacquer is prepared by mixing the following ingredients in the amounts indicated:

| Coating B | |
|---|---|
| Ingredient | Amount (g) |
| Methylene chloride | 36.0 |
| Isopropanol | 4.0 |
| Cellulose acetate butyrate described in Example 13 | 4.53 |
| Phenanthrenequinone | 0.045 |
| $CF_3(CF_2CF_2)_{17}CH_2CH_2-O-\overset{\overset{O}{\|}}{C}(CH_2)_{16}CH_3$ | 0.038 |
| 3-Methoxy-4-octamidophenyl-bis(4-diethylamino-2-methylphenyl) methane | 0.088 |
| Trans-3-hydroxy-2-(p-diethylaminobenzyl)indanone | 0.038 |
| N-ethyl-p-toluenesulfonamide | 0.98 |
| Dodecylbenzenesulfonic acid | 0.493 |
| Triethanolamine triacetate | 1.66 |
| o-Phenylphenol condensed with average of ~2.25 mols ethylene oxide | 1.19 |
| Silica gel described in Example 13 | 0.30 |
| Hexaphenylbiimidazole No. 3, Example 11 | 0.30 |

The coating lacquer is coated on Schweitzer 32-HG paper with a 032 wire-wound rod, and dried with hot air. Exposure to BLB fluorescent lamps in a contact printer, at an irradiance of 6 mw/cm$^2$ through a silver negative generates black images with a density of 1.22. Substantially no color develops when the coating is exposed to 80 foot candles (~860 meter candles) of cool white fluorescent light for 1 hour, but a whitening of the yellow areas is noticed. The OD$_{max}$ is 2.1; the OD$_{min}$ is 0.15.

EXAMPLE 15

This example illustrates a fast photofix composition.

A coating solution is prepared by mixing the following ingredients in the amounts indicated:

| Ingredient | Amount (g) |
|---|---|
| Methylene chloride | 107.0 |
| Isopropanol | 6.8 |
| Cellulose acetate butyrate described in Example 13 | 11.3 |
| Pyrenequinone as described in | |

-continued

| Ingredient | Amount (g) |
|---|---|
| Example 13 | 0.0113 |
| Phenanthrenequinone | 0.225 |
| $CF_3(CF_2CF_2)_{17}CH_2CH_2-O-\overset{\overset{O}{\|}}{C}(CH_2)_{16}CH_3$ | 0.101 |
| 7-Diethylamino-4-methylcoumarin | 0.262 |
| N-Ethyl-p-toluenesulfonamide | 2.63 |
| Dodecylbenzenesulfonic acid | 3.375 |
| Triethanolamine triacetate | 4.123 |
| o-Phenylphenol condensed with average of ~2.25 mols ethylene oxide | 3.0 |
| Silica gel described in Example 14 | 0.79 |
| Hexaphenylbiimidazole No. 3, Example 11 | 0.64 |

The solution is applied onto Schweitzer 32-HG paper with a 010 coating bar, at a dry coating weight of 82 mg/dm$^2$. Exposure of the dried coating ultraviolet radiation from a bank of BLB lamps, with an irradiance of 9 mw/cm$^2$ for 20 seconds produces an image density of 0.9 (reflectance). A positive image results when the coating is exposed through a lithographic negative for 10 seconds in a bank of SDZ fluoroescent lamps, followed by a 5-second exposure to the BLB lamps. An image density of 0.8, with a background of 0.1 is observed.

A slightly lower image density results when 0.51 g of the hexaphenylbiimidazole is used instead of 0.64 g; the image density for coatings of about 80 mg/dm$^2$ is 0.7.

When 2,2'-bis(o-chlorophenyl)-4,4',5,5'-tetrakis-(m-methoxyphenyl)-biimidazole (control)* is used as photoinitiator, 1.28 g is required to achieve a similar level of performance as is achieved with the lower levels of the hexaphenylbiimidazole described above.

* On a molecular weight basis the hexaphenylbiimidazole of this example is 2.2 times better than the control hexaphenylbiimidazole.

EXAMPLE 16

This example illustrates the preparation of a heat-fix formulation.

The following ingredients are mixed together in the amounts indicated:

| Ingredient | Amount (g) |
|---|---|
| Acetone | 250.0 |
| Cellulose acetate butyrate described in Example 11 | 60.0 |
| 3,4-Dimethoxyphenyl-bis(4-diethylamino-2-methylphenyl)methane | 2.48 |
| p-Toluenesulfonic acid | 2.06 |
| Di-t-butyl hydroquinone adduct with dihydropyran, mol wt 274 | 2.88 |
| p-Cresol-ethylene oxide adduct, mol wt is ~170 | 18.0 |
| Hexaphenylbiimidazole No. 3, Example 11 | 0.40 |

The formulation is coated with a 020 bar onto Schweitzer Sub 14 paper and dried with air. It is imaged for 20 seconds by exposure through a negative with BLB ultraviolet lamps to give an image density of 1.09. The coated paper is brought into contact with an aluminum block heated to 300° F. (149° C.) for 15 seconds. Subsequent exposure to cool white fluorescent lamps [680 ft. candles (~7320 meter candles) intensity] for 2.75 hours produces no further color, indicating that the photoinitiator is deactivated; background density is 0.05.

EXAMPLE 17

This example illustrates a photopolymerizable composition containing a hexaphenylbiimidazole of the invention as a photoinitiator.

A prepolymer is prepared as follows: to 300 g of an aliphatic diisocyanate polymer, specific gravity 1.07, Hylene ® W, E. I. du Pont de Nemours and Company, Wilmington, DE stirred under nitrogen, is added 149 g of 2-hydroxyethylmethylmethacrylate and 0.001 g of phenothiazine. Their reaction mixture is heated to 55° C., followed by two hours at 60° C.

The prepolymer is present in the following mixture:

| Ingredient | Amount (g) |
|---|---|
| Prepolymer (binder) | 10.0 |
| Hexaphenylbiimidazole No. 3, Example 11 | 0.05 |
| Michler's ketone (initiator) | 0.02 |
| N-Phenylglycine (hydrogen donor) | 0.04 |
| Methylene chloride (solvent) | 5.00 |

The mixture is stirred in the dark, and then is cast on a 0.003 inch (0.076 mm) thick polyethylene terephthalate film. After air-drying the coating is covered with a 0.001 inch (0.025 mm) thick polyethylene terephthalate film, and the element formed is exposed to BLB ultraviolet lamps for 60 seconds. A tack-free photopolymer is observed.

A similar coating is made on a glossy paper with a 040 coating bar. It is overlaid with thin polyethylene terephthalate film and is exposed to give a tack-free coating after 60 seconds.

EXAMPLE 18

A solution is prepared as follows:

| Ingredient | Amount (g) |
|---|---|
| 1. Trimethylolpropane-trimethacrylate (monomer) | 16.796 |
| 2. Monolauryl ether of tetra(oxyethylene) glycol (plasticizer) | 5.599 |
| 3. Methylene chloride (solvent) | 441.600 |
| 4. (a) Copolymer of methylmethacrylate and ethylacrylate, mol wt 500,000 determined by gel permeation chromatography, Brookfield viscocity 10% in toluene, 25° C., 60 rpm, #1 spindle is 15 to 45 cps (binder) | 25.529 |
| (b) 2,2'-Dihydroxy-4-methoxy-benzophenone (UV absorber) | 0.045 |
| (c) 2-Mercaptobenzothiazole (chain transfer agent) | 0.448 |
| 5. (a) 2-(Stilbyl-4")-(naphtho-1',4,5)-1,2,3-triazole-2'-sulfonic acid phenyl ester (UV absorber) | 0.112 |
| (b) 7-(4'-Chloro-6'-diethylamino-1',3',5'-triazine-4'-yl)amino-3-phenyl coumarin (UV absorber) | 0.546 |

To a 10 g (1.0 g solids) aliquot of the above solution is added 0.183 g of one of the hexaphenylbiimidazole compounds of Example 11, i.e., 1, 2 or 3. The solutions are coated using a 0.075 mm knife onto sub-coated polyethylene terephthatate film, 0.075 mm in thickness, are air dried for about 10 minutes, and are laminated with a polyethylene terephthalate cover film, 0.025 mm in thickness. The photopolymer films having a coating weight of about 46 mg/dm² are each exposed for 2 seconds using the following sources:

(1) 2000 watt pulsed Xenon manufactured by nuArc Company, Chicago, Illinois [17 inches (43.18 cm) from vacuum frame].

(2) A bank of 10 black light blue fluorescent lamps manufactured by GTE Sylvania 18T8/BLB/40/180° maintained 2 inches (5.08 cm) from pressure held frame. After exposure through a $\sqrt[3]{2}$ step wedge image the cover film is removed and colored toner is applied to each. The following results are obtained:

| Hexaphenylbiimidazole | Exposure Source | Photospeed* |
|---|---|---|
| 1 | 1 | 5–12 |
| 2 | 1 | 5–12 |
| 3 | 1 | 7–15 |
| 1 | 2 | 5–11 |
| 2 | 2 | 5–11 |
| 3 | 2 | 6–14 |

*$\sqrt[3]{2}$ (step wedge) step totally polymerized to step totally unpolymerized.

The samples (3) using a hexaphenylbiimidazole compound of the invention are on the average about 1.8 and 1.67 faster than the controls (1 and 2) using exposure source 1 and 2, respectively.

EXAMPLE 19

This example illustrates a high speed imaging system.

A coating solution is prepared by mixing the following ingredients in the amounts indicated:

| Ingredient | Amount (g) |
|---|---|
| Acetone | 65.0 |
| Di-i-propylamine | 1.0 |
| p-Formylphenoxyacetic acid | 0.8 |
| o-Formylphenoxyacetic acid | 0.8 |
| Nonylphenoxypoly(etheneoxy)-ethanol | 1.0 |
| Tricresyl phosphate | 1.0 |
| Leuco Crystal Violet (C.I. 42555) | 0.4 |
| Benzophenone | 0.6 |
| Ethylenediamine tetracetic acid | 1.0 |
| Cellulose acetate butyrate described in Example 13 | 6.0 |
| 1-Phenylpyrazolidine-3-one | 0.048 |
| Hexaphenylbiimidazole No. 3, Example 11 | 0.32 |

The solution is coated on Schweitzer 32-HG paper with a 0015 coating bar, and is exposed with BLB ultraviolet lamps for 10 seconds to give a reflectance optical density of 1.25. A 60-second exposure gives an optical density of 1.47. A 30-second exposure to visible light (SDZ lamps) gives an optical density of 1.36.

EXAMPLES 20 TO 22

Three coating solutions are prepared by mixing the following ingredients in the amounts indicated:

| Ingredient | Ex.20 | Ex.21 | Ex.22 |
|---|---|---|---|
| Methylene chloride | 432.0 | 530.0 | 514.0 |
| Isopropanol | 48.0 | 50.0 | 56.0 |
| Dodecylbenzenesulfonic acid | 4.31 | — | — |
| Tris(p-diethylamino-o-tolyl) methane | 1.65 | — | 2.14 |
| N-Ethyl-p-toluenesulfonamide | 17.1 | 22.1 | — |
| o-Phenylphenol condensate with average of ~2.25 mols ethyleneoxide(plasticizer) | 14.1 | 18.3 | 32.2 |

-continued

| Ingredient | Amount (g) | | |
|---|---|---|---|
| | Ex.20 | Ex.21 | Ex.22 |
| Mixture of ~83% 1,6- and 17% 1,8-pyrenequinones | 0.0234 | — | — |
| 9,10-Phenanthrenequinone | 0.826 | 0.273 | — |
| Triethanolamine triacetate | 11.95 | 15.5 | — |
| Silica gel of 9 μ average particle diameter surface area of 675 meters squared per gram, bulk density ~465 kg/m³ | 3.60 | 6.3 | — |
| Cellulose acetate butyrate as described in Example 13 | 62.4 | 80.0 | — |
| CF$_3$(CF$_2$CF$_2$)$_{17}$CH$_2$CH$_2$—O—$\overset{\overset{O}{\|}}{\underset{\|}{C}}$—H$_3$C(H$_2$C)$_{16}$ | 0.12 | — | — |
| p-Toluenesulfonic acid | — | 3.23 | 2.24 |
| 3-Methoxy-4-octamido-phenyl-bis(4-diethyl-amino-2-methylphenyl) methane | — | 2.01 | — |
| Trans-3-hydroxy-2-(p-diethylaminobenzyl)-indanone | — | 0.90 | — |
| Cellulose acetate butyrate described in Example 11 | — | — | 92.0 |

Aliquots, 15.4 g for Example 20, 15.15 g for Example 21 and 13.2 g for Example 22, are taken and to each aliquot is added $1.2 \times 10^{-4}$ mol of a hexaphenylbiimidazole set forth below in Table 8. After stirring for at least 30 minutes, the solutions are coated on Schweitzer 32-HG paper or 0.002 inch thick (0.05 mm) polyethylene terephthalate film with a 032 wire-wound rod. The coatings are air-dried overnight, and are exposed and Examples 20 and 21 formulations are fixed. Example 22 formulation, coating weights are the same as corresponding formulation of Example but are not photodeactivated. In Table 8 the exposure sources are:

EXAMPLES 20 AND 21

BLB fluorescent lamps (BLB max) through a step tablet for 90 seconds with an irradiance of about 8 mw/cm², followed by a 90-second photodeactivation exposure using GTE Sylvania lamps which peak at 440–450 nm. Positive images (Pos. Im.) are prepared by initially exposing through a litho negative image for 90 seconds with the GTE Sylvania lamps followed by a 10-second exposure to the BLB lamps after removing the negative.

EXAMPLE 22

(a) BLB fluorescent lamps through a step tablet for 90 seconds with an irradiance of about 8 mw/cm²;

(b) SDZ fluorescent lamps, directly for 60 seconds with an irradiance of about 3 mw/cm²;

(c) as in (b) but an interposed weatherable polyethylene terephthalate film is placed between the exposure source and the photosensitive coating.

The density readings are measured with a MacBeth Quantalog ® densitometer for a visual density reading (reflectance mode).

For the film coatings a white Morest ® card as used for pigment drawdown is employed under the coated films. The steps column in Table 8 refers to the maximum number of steps totally polymerized.

TABLE 8

| Dimer (See Tables 5 & 6) | Mols × 10³ | Ctg. Wt. (mg/dm²) | BLB Max Reflect | Pos. Im. Steps | $D_{max}/D_{min}$ Reflect |
|---|---|---|---|---|---|
| Blue (Ex. 20) | | | | | |
| 1 | 0.119 | 157 | 1.32 | 21 | 1.53/0.12 |
| 2 | 0.120 | 156 | 1.21 | 22 | |
| 4 | 0.118 | 145 | 1.35 | 21 | 1.46/0.18 |
| 5 | 0.120 | 184 | 1.32 | 21 | |
| 6 | 0.118 | 167 | 1.35 | 22 | |
| 7 | 0.120 | 185 | 1.20 | 20 | 1.25/0.12 |
| 8 | 0.120 | 151 | 1.41 | 23 | 1.28/0.13 |
| 9 | 0.119 | 169 | 1.24 | 22 | |
| 10 | 0.100 | 146 | 1.21 | 20 | 1.24/0.1 |
| Control 1 (Example 11) | 0.118 | 164 | 0.88 | 19 | |
| Control 2 (Example 11) | 0.118 | 210 | 0.99 | 15 | 0.97/0.14 |
| Black (Ex. 21) | | | | | |
| 1 | 0.119 | 133 | 1.29 | 21 | 1.32/0.12 |
| 2 | 0.120 | 131 | 1.08 | 21 | 1.17/0.11 |
| 4 | 0.118 | 141 | 1.34 | 25 | 1.30/0.16 |
| 5 | 0.120 | 133 | 1.32 | 22 | 1.29/0.14 |
| 6 | 0.118 | 149 | 1.12 | 22 | |
| 7 | 0.120 | 136 | 1.21 | 20 | 1.23/0.11 |
| 8 | 0.120 | 185 | 1.08 | 20 | |
| 9 | 0.119 | 138 | 1.03 | 20 | |
| 10 | 0.100 | 165 | 0.77 | 20 | |
| Control 1 (Example 11) | 0.118 | 131 | 1.21 | 17 | 1.20/0.17 |
| Control 2 (Example 11) | 0.118 | 140 | 0.53 | 11 | 0.51/0.12 |

| Dimer (See Tables 5 & 6) | Mols × 10³ | BLB (a) Max Reflect | Steps | SDZ (b) Reflect | SDZ (c) Reflect |
|---|---|---|---|---|---|
| Blue-No Fix (Ex. 22) | | | | | |
| 1 | 0.119 | 1.60 | 24 | 1.52 | 0.73 |
| 2 | 0.120 | 1.58 | 24 | 1.59 | 0.76 |
| 3 | 0.120 | 1.72 | 24 | 1.30 | 0.53 |
| 4 | 0.118 | 1.50 | 25 | 1.46 | 0.72 |
| 5 | 0.120 | 1.70 | 25 | 1.60 | 0.71 |
| 6 | 0.118 | 1.49 | 23 | 1.35 | 0.58 |
| 7 | 0.120 | 1.48 | 24 | 1.44 | 0.57 |
| 8 | 0.120 | 1.51 | 23 | 1.31 | 0.77 |
| 9 | 0.119 | 1.50 | 23 | 1.35 | 0.47 |
| 10 | 0.100 | 1.44 | 25 | 1.40 | 0.66 |
| Control 1 (Example 11) | 0.118 | 1.72 | 24 | 1.13 | 0.33 |
| Control 2 (Example 11) | 0.118 | 1.65 | 20 | 1.19 | 0.41 |

EXAMPLE 23

The following stock solution is prepared:

| Ingredient | Amount (g) |
|---|---|
| 2-(Stilbyl-4″)-(naphtho-1′,4,5)-1,2,3-triazole-2′-sulfonic acid Phenyl ester (UV absorber) | |
| 7-(4′-Chloro-6′-diethylamino-1′,3′,5′-triazine-4′-yl)amino-3-phenyl coumarin (UV absorber) | 3.88 |
| Trimethylolpropanetrimethacrylate | 139.50 |
| Polyoxyethylated trimethylol propane Triacrylate, mol wt 1000–1200 | 31.00 |
| Monolauryl ether of tetra(oxyethylene)glycol (plasticizer) | 31.00 |
| Polymethylmethacrylate, Very high mol wt, Inherent Viscosity 1.37 determined in 0.25 g of CHCl$_3$, 25° C. using a No. 50 | |

-continued

| Ingredient | Amount (g) |
| --- | --- |
| Cannon-Fenske Viscometer | 127.10 |
| Polyvinyl acetate, ~86 monomer units chain length | 49.60 |
| 2,2'-Dihydroxy-4-methoxy-benzophenone | 0.31 |
| Hydroquinone | 0.20 |
| 2-Mercaptobenzoxazole | 2.79 |
| Methylene chloride | 3476.00 |

To 38.6 g aliquots of this solution are added $9.4 \times 10^{-5}$ mol of each of the photoinitiators listed in Table 6 (Controls as solids, Dimer 1 as 31% solution in methyl ethyl ketone, the rest as 15% solutions in methylene chloride). The solutions are stirred and are coated on polyethylene terephthalate supports using a 0.003 inch (0.076 mm) knife to yield a coating 0.0003 inch (0.0076 mm) in thickness. After air drying for about 10 minutes, a polypropylene cover sheet 0.00075 inch (0.019 mm) in thickness is applied using a squeegee. The coated films are exposed simultaneously through a $\sqrt[3]{2}$ step tablet to each of two radiation sources:

(1) 2000-watt pulsed xenon lamp in a nuArc ® flip-top exposure frame, 20 seconds, 17 inches (43.18 cm) from the films in the pressure frame.

(2) Series of SDZ fluorescent lamps with an output of 450 ft.-candles (4840 meter-candles), 60 seconds, 2 inches (5.08 cm) from films in the pressure frame.

After exposure the cover sheets are removed and a colored toner is applied by dusting each exposed film. The following results are obtained, Table 9 illustrates radiation source (1) and Table 10 radiation source (2).

TABLE 9

| Dimer (See Tables 5 and 6) | Photospeed* | Photospeed** |
| --- | --- | --- |
| 1 | 7 to 10 | 1.63 |
| 2 | 7 to 12 | 3.0 |
| 3 | 5 to 9 | 1.13 |
| 4 | 7 to 10 | 1.63 |
| 5 | 7 to 11 | 1.79 |
| 6 | 7 to 11 | 1.79 |
| 7 | 7 to 9 | 1.50 |
| 8 | 8 to 11 | 2.05 |
| 9 | 6 to 10 | 1.42 |
| 10 | 6 to 9 | 1.29 |
| Control 1, Example 11 | 5 to 11 | |
| Control 2, Example 11 | 4 to 9 | 1.00 |

*Step totally polymerized to step totally unpolymerized
**Speed factor relative to Control 2 which is 1.0; speed factor equals [[antilog [(step no. experimental − step no. control 2)

left value times log ( $\sqrt[3]{2}$ )] + antilog
[(step no. experimental − step no. Control 2)

right value × log $\sqrt[3]{2}$ )]] divided by 2.

TABLE 10

| Dimer (See Tables 5 and 6) | Photospeed* | Photospeed** |
| --- | --- | --- |
| 1 | 12 to 14 | 1.13 |
| 2 | 13 to 15 | 1.42 |
| 3 | 11 to 14 | 1.00 |
| 4 | 13 to 15 | 1.42 |
| 5 | 12 to 15 | 1.26 |
| 6 | 14 to 16 | 1.79 |
| 7 | 13 to 15 | 1.42 |
| 8 | 14 to 16 | 1.79 |
| 9 | 13 to 15 | 1.42 |
| 10 | 12 to 15 | 1.26 |
| Control 1, Example 11 | 11 to 14 | |

TABLE 10-continued

| Dimer (See Tables 5 and 6) | Photospeed* | Photospeed** |
| --- | --- | --- |
| Control 2, Example 11 | 11 to 14 | 1.00 |

*Step totally polymerized to step totally unpolymerized
**Speed factor relative to Control 2 which is 1.0. Speed factor is determined by formula beneath Table 9.

EXAMPLE 24

The following stock solution is prepared:

| Ingredient | Amount (g) |
| --- | --- |
| Michler's ketone | 5.0 |
| Trimethylolpropane triacrylate | 145.0 |
| Triethyleneglycol diacetate | 20.0 |
| Tricresyl phosphate | 20.0 |
| Dioctylphthalate | 20.0 |
| Peroxide-initiated polymethylmethacrylate, high mol wt, inherent viscosity 1.37 determined in 0.25 g of CHCl₃, 25° C. using a No. 50 Cannon-Fenske Viscometer | 20.0 |
| Peroxide-initiated polymethylmethacrylate, low mol wt, inherent viscosity 0.21 determined in 0.25 g of CHCl₃, 25° C. using a No. 50 Cannon-Fenske Viscometer | 145.0 |
| Victoria Pure Blue BO (CI 42595) | 0.15 |
| Benzotriazole | 1.0 |
| Tris-(p-diethylamino-o-tolyl)methane | 1.5 |
| Tris-(p-dimethylaminophenyl)-methane | 0.5 |
| Methylene chloride | 2709.0 |

To 31.9 aliquots of this solution are added $3.03 \times 10^{-4}$ mol of each of the photoinitiators listed in Table 6 (Controls as solids, Dimer 1 as 31% solution in methyl ethyl ketone, the rest as 15% solutions in methylene chloride). The solutions are stirred and are coated on polyethylene terephthalate films using a 0.010 inch (0.25 mm) knife to yield a coating 0.0015 inch (0.038 mm) in thickness. After air drying for 30 minutes, the films are laminated onto precleaned copper circuit boards at 40 psi (2.81 kg/sq cm) pressure and 220° F. (105° C.). The coated films are exposed for 30 units (about 90 seconds) through a 21 step $\sqrt{2}$ step tablet on a Berkey-Ascor unit (to a 2 kw Addalux ® mercury photopolymer type lamp). After the exposure, the polyethylene terephthalate films are removed and the unexposed areas are washed out during a one-minute development cycle in a Riston ® processor using chlorothene. The following results are obtained:

TABLE 11

| Dimer (See Tables 5 and 6) | Photospeed* | Photospeed** |
| --- | --- | --- |
| 1 | 6 to 8 | 1.71 |
| 2 | 6 to 8 | 1.71 |
| 3 | 6 to 7 | 1.41 |
| 4 | 7 to 8 | 2.0 |
| 5 | 6 to 8 | 1.71 |
| 6 | 5 to 6 | 1.0 |
| 7 | 5 to 6.5 | 1.09 |
| 8 | 7 to 8 | 2.0 |
| 9 | 6 to 7 | 1.41 |
| 10 | 6 to 8 | 1.71 |
| Control 1, Example 11 | 3 to 5 | |

TABLE 11-continued

| Dimer (See Tables 5 and 6) | Photospeed* | Photospeed** |
|---|---|---|
| Control 2, Example 11 | 5 to 6 | 1.00 |

*Step totally polymerized to step totally unpolymerized.
**Speed factor relative to Control 2 which is 1.0. Speed factor is determined by formula beneath Table 9 except that $\log(\sqrt[3]{2})$ is replaced by $\log(\sqrt{2})$.

It is known that imidazolyl radicals exhibit unique signals when examined in an esr spectrometer; diminution of the signals indicates disappearance of the radical to give the starting dimer. It is further known that many biimidazole compounds on photolysis give rise to colored free radicals. In the absence of exciting radiation, these radicals recombine to give the starting dimer. This dimerization process may be speeded up by heat or increased plasticization of the medium. Techniques for measuring absorption spectra of the radicals or colorometric measurements of films or treated papers may thus be employed to make comparisons in the lifetime of imidazolyl radicals.

The following Examples illustrate the increased radical lifetime of radicals formed from imidazolyl dimers of this invention.

EXAMPLE 25

Electron Spin Resonance (esr) Measurements (A) Solutions of 0.01 molarity in methylene chloride are made with Control 1 (Example 11) and hexaphenylbiimidazole No. 3, Example 11. These are inserted in 3.0 mm (ID) Pyrex ® tubes inside the cavity of a Bruker ® BR420 esr spectrometer, and are exposed to several flashes with an electronic flashgun (Exposure Source 3 of Table 7). The signal generated by the radical is recorded over a period of time, and disappears completely after 200 seconds for the control. Signal strength of one-third the original is detected after more than 2000 seconds for hexaphenylbiimidazole No. 3, Example 11, a lifetime of over 10 times greater in solution for the radicals derived from the hexaphenylbiimidazole of this invention.

(B) Films are prepared by coating a lacquer containing 0.96 g cellulose acetate butyrate described in the photosensitive compositions of Examples 1 to 10, 0.15 g hexaphenylbiimidazole, and 8.0 g methylene chloride onto a polyethylene terephthalate film using a 032 coating bar. The film weight is approximately 0.056 g/dm². A film made with hexaphenylbiimidazole No. 3, Example 11, is inserted in a 4.0 mm (ID) Pyrex ® tube, and is exposed for several minutes with ultraviolet light. The sample is placed in the cavity of the above-described esr instrument, and the signal is recorded. After 66 hours the sample is scanned again. It retains 40% of the original signal strength. A similarly exposed film made with Control 1 (Example 11) shows a signal initially but shows no signal after 16 hours, indicating appreciably longer radical lifetime in films prepared containing the hexaphenylbiimidazole of this invention.

The solution (A) containing hexaphenylbiimidazole No. 3, Example 11, shows a single esr absorption 7 gauss wide with G-factor of 2.0028. This signal is also observed in irradiated films (B) except that a slightly broader line width of 8 gauss is found.

EXAMPLE 26

(A) Stability of Radicals By Optical Measurements

Films are prepared as described in Example 25 (B) except that the below listed hexaphenylbiimidazole compounds are used. The films are scanned in a Cary Model 17 spectrophotometer from 700 nm to 300 nm. Samples are then irradiated with ultraviolet light from BLB lamps for 110 seconds. Exposed samples are then returned to the spectrophotometer for additional scanning over the same wavelength range. The scanning is repeated after 22 hours. Approximately the same length of time is employed in handling each sample. Scanning from 700 to 300 nm takes about 4 minutes.

A wavelength is selected at which there is a maximum difference between the exposed and unexposed film sample. The 22-hour old sample shows a decrease in optical density at that wavelength. The decrease in radical concentration is determined according to the formula:

$$\text{Loss in radical concentration } (R') = \frac{OD_{IRR} - OD_{22}}{DD_{DRR} - OD_{UN}}$$

where $OD_{IRR}$ is the optical density of the film after irradiation, $OD_{22}$ is the optical density of the film after 22 hours, and $OD_{UN}$ is the optical density of the unirradiated film.

| Sample | Wavelength (nm) | Formula | Loss (%) |
|---|---|---|---|
| Control 1, Example 11 | 380 | $\frac{0.29 - 0.23}{0.29 - 0.23}$ | 100 |
| Control 2, Example 11 | 360 | $\frac{0.38 - 0.23}{0.38 - 0.18}$ | 75 |
| Compound 10, Tables 5 and 6 | 460 | $\frac{0.215 - 0.12}{0.215 - 0.065}$ | 63 |
| Compound 3, Tables 5 and 6 | 400 | $\frac{0.75 - 0.44}{0.75 - 0.21}$ | 57 |
| Compound 1, Tables 5 and 6 | 400 | $\frac{0.90 - 0.55}{0.90 - 0.23}$ | 52 |

These data show that the compounds of the invention have longer radical life versus the controls. The differences between the controls and hexaphenylbiimidazole compounds of this invention indicate that electronic effects, arising from substituents, as well as steric factors which may be present, as shown by 4-phenyl ortho-substituted compounds of this invention influence radical life.

(B) Colorometric Measurements

Samples of the above films are irradiated for 90 seconds with a light source containing BLB lamps, with an irradiance of about 9 mw/cm². Reflectance measurements are made on the films prior to exposure, immediately after exposure, 2 hours after exposure and 67 hours later. Reflectance readings are made with the film over a black tile, using a Photomatch ® 300 colorimeter; the readings are $\Delta L$ (lighter/darker), $\Delta a$ (redder/greener) and $\Delta b$ (yellower/bluer). The values for $\Delta E$ set forth in Table 12 below are derived from the square root of the sum of the squares $(\Delta L^2 + \Delta a^2 + \Delta b^2)$ and give an approximation of the overall change of color of the film sample. It is observed that the control hexaphenylbiimidazoles form relatively little color after exposure which disappeared after 2 hours. All film samples of this invention retained color longer. This confirms that the hexaphenylbiimidazole compounds of this invention have longer radical life.

TABLE 12

| Film Sample (see Tables 5 and 6) | Before Exposure | After Exposure | 2 Hrs. After Exposure | 67 Hrs. After Exposure |
|---|---|---|---|---|
| | | Change in Δ E Values | | |
| 1 | 1.5 | 6.2 | 5.1 | 5.1 |
| 2 | 1.3 | 5.0 | 3.3 | 3.1 |
| 3 | 0.6 | 5.0 | 2.3 | 1.8 |
| 4 | 1.4 | 6.1 | 4.4 | 4.4 |
| 5 | 1.6 | 5.7 | 3.7 | 2.8 |
| 6 | 1.7 | 3.1 | 2.6 | 2.6 |
| 7 | 1.8 | 5.2 | 3.3 | 2.8 |
| 8 | 1.6 | 5.3 | 4.3 | 4.3 |
| 9 | 1.5 | 5.1 | 3.5 | 3.5 |
| 10 | 1.3 | 6.0 | 4.7 | 4.7 |
| Control 1, Example 11 | 1.1 | 1.9 | 1.1 | — |
| Control 2, Example 11 | 1.5 | 2.3 | 1.0 | — |

(C) Radical Recombination By Heating

A 15% solution of hexaphenylbiimidazole No. 3, Example 11, in methylene chloride is spotted on filter paper, and after color formation by ultraviolet irradiation, a portion of the colored pattern is placed in an oven set at 85°–90° C.

Initially, before exposure, optical density is 0.38; after a 90 second exposure the optical density is 1.40.

| Time | Room Temp. (O.D.) | Oven Heated (O.D.) |
|---|---|---|
| 1 hour | 1.37 | 1.13 |
| 1.75 hours | 1.34 | 1.06 |
| 2 hours | 1.33 | 1.02 |
| 20 hours | 1.20 | 0.64 |
| 44 hours | 1.16 | 0.56 |

This shows that the radicals formed by the exposure to ultraviolet light can be made to recombine at elevated temperatures over an extended period. Reexposure of the heated sample to ultraviolet light regenerates the color to an optical density of 1.22.

I claim:

1. A photoimaging composition consisting essentially of an admixture of 0.1 to 10% by weight of solids of a 2,4,5-triphenylimidazolyl dimer of the formula

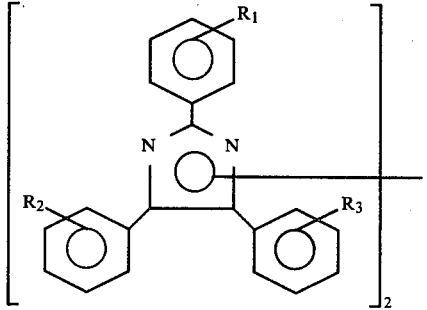

wherein
R₁ is 2-bromo, 2-chloro, 2-fluoro, 2-alkyl of 1 to 4 carbon atoms and 2,4-dichloro;
R₂ is 2-bromo, 2-chloro, 2-fluoro, 4-chloro, 2-alkyl of 1 to 4 carbon atoms, 2-cyano, and 2-alkoxy wherein the alkyl radical is of 1 to 4 carbon atoms; and
R₃ is 3,4-dimethoxy, 3,4-diethoxy, 2,3-dimethoxy, 2,4,6-trimethoxy, 4-alkoxy wherein the alkyl radical is of 1 of 4 carbon atoms and 3,4-methylenedioxy; the imidazolyl dimer having an extinction coefficient determined in methylene chloride at $10^{-5}$ to $10^{-3}$ mol/liter at 350 nm of at least 4000 liters/mol-cm and at 400 nm of at least 250 liters/mol-cm; and 0.1 to 5.0 percent by weight of solids of leuco dye that is oxidizable to dye by the imidazolyl radicals; and optionally an acid or acid-supplying compound and an energy-transfer dye.

2. A photoimaging composition according to claim 1 having present at least one leuco dye which has one to two removable hydrogens, the removal of which forms a differently colored compound, with the proviso that when the leuco form has only one removable hydrogen and the resultant dye is cationic, there is also present a mineral acid, organic acid or acid-supplying compound which forms a salt with the leuco form of the dye.

3. A photoimaging composition according to claim 2 wherein the leuco dye is the salt of an acid in leuco form of a triphenylmethane dye having, in at least two of the phenyl rings positioned para to the methane carbon atom, a substituent selected from the group consisting of amino, and C₁ to C₄ dialkyl amino groups, the acid being a mineral acid, an organic acid, or an acid-supply compound.

4. A photoimaging composition according to claim 1 wherein a film-forming polymeric binder is present.

5. A photoimaging composition according to claim 4 wherein the polymeric binder is cellulose acetate butyrate.

6. A photoimaging composition according to claim 1 wherein the 2,4,5-triarylimidazolyl compound is 2,2',4,4'-tetrakis(o-chloro-phenyl)-5,5'-bis(m,p-dimethoxyphenyl)-biimidazole dimer.

7. A photoimaging composition according to claim 1 wherein a precursor of hydroquinone which leads to the formation of hydroquinone by heat is present in the admixture.

8. A photoimaging composition consisting essentially of an admixture of 0.1 to 10% by weight of solids of a 2,4,5-triphenylimidazolyl dimer of the formula

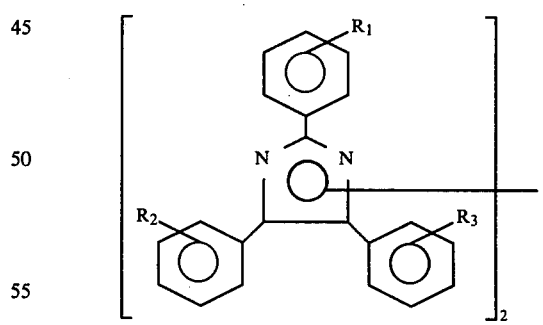

wherein
R₁ is 2-bromo, 2-chloro, 2-fluoro, 2-alkyl of 1 to 4 carbon atoms and 2,4-dichloro;
R₂ is 2-bromo, 2-chloro, 2-fluoro, 4-chloro, 2-alkyl of 1 to 4 carbon atoms, 2-cyano, and 2-alkoxy wherein the alkyl radical is of 1 to 4 carbon atoms; and
R₃ is 3,4-dimethoxy, 3,4-diethoxy, 2,3-dimethoxy, 2,4,6-trimethoxy, 4-alkoxy wherein the alkyl radical is of 1 to 4 carbon atoms and 3,4-methylenedioxy; the imidazolyl dimer having an extinction coefficient determined in methylene chloride at $10^{-5}$ to $10^{-3}$ mol/liter at 350 nm of at least 4000 liters/mol-cm and at 400 nm of at least 250 liters/mol-cm; 0.1 to 5.0 percent by weight of solids of leuco dye that is oxidizable to dye by the imidazolyl radicals; a redox couple of a photoactivatable oxidant component and a reductant component; and optionally an acid or acid-supplying compound and an energy-transfer dye.

9. A photoimaging composition according to claim 8 wherein the photoactivatable oxidant component is a polynuclear quinone absorbing principally in the 430 nm to 550 nm region.

10. A photoimaging composition according to claim 8 wherein the reductant component is an acyl ester of triethanolamine of the formula

where R is alkyl of 1 to 4 carbon atoms.

11. A photoimaging composition according to claim 8 having present at least one leuco dye which has one to two removable hydrogens, the removal of which forms a differently colored compound, with the proviso that when the leuco form has only one removable hydrogen and the resultant dye is cationic, there is also present a mineral acid, organic acid or acid-supplying compound which forms a salt with the leuco form of the dye.

12. A photoimaging composition according to claim 11 wherein the leuco dye is the salt of an acid in leuco form of a triphenylmethane dye having, in at least two of the phenyl rings positioned para to the methane carbon atom, a substituent selected from the group consisting of amino, and $C_1$ to $C_4$ dialkyl amino groups, the acid being a mineral acid, an organic acid, or an acid-supplying compound.

13. A photoimaging composition according to claim 8 wherein a film-forming polymeric binder is present.

14. A photoimaging composition according to claim 13 wherein the polymeric binder is cellulose acetate butyrate.

15. A photoimaging composition according to claim 8 wherein the 2,4,5-triarylimidazolyl compound is 2,2',4,4'-tetrakis(o-chloro-phenyl)-5,5'-bis(m,p-dimethoxyphenyl)-biimidazole dimer.

16. A photoimaging composition according to claim 8 wherein a precursor of hydroquinone which leads to the formation of hydroquinone by heat is present in the admixture.

* * * * *